United States Patent [19]

Das et al.

[11] Patent Number: 4,542,156

[45] Date of Patent: Sep. 17, 1985

[54] 7-OXABICYCLOHEPTANE SUBSTITUTED PROSTAGLANDIN ALCOHOLS AND THEIR USE IN THE TREATMENT OF THROMBOLYTIC DISEASE

[75] Inventors: Jagabandhu Das, Plainsboro; Martin F. Haslanger, Lambertville, both of N.J.

[73] Assignee: E. R. Squibb & Sons, Inc., Princeton, N.J.

[21] Appl. No.: 604,342

[22] Filed: Apr. 26, 1984

[51] Int. Cl.[4] .................. A61K 31/34; A61K 31/557; C07D 307/00

[52] U.S. Cl. .................................... 514/469; 549/463

[58] Field of Search ....................... 549/463; 424/285; 514/469

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS

| | | |
|---|---|---|
| 0043292 | 8/1982 | European Pat. Off. . |
| 2039909 | 8/1980 | United Kingdom . |

*Primary Examiner*—Henry R. Jiles
*Assistant Examiner*—Bernard I. Dentz
*Attorney, Agent, or Firm*—Lawrence S. Levinson; Burton Rodney

[57] ABSTRACT

7-Oxabicycloheptane substituted prostaglandin alcohols are provided having the structural formula

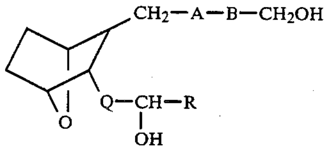

wherein A is $-CH{=}CH-(CH_2)_n-$ or $(CH_2)_q$; B is a single bond or $-CH{=}CH-$; n is 1 to 5; q is 1 to 6; Q is $-CH{=}CH-$ or $(CH_2)_2$; and R is lower alkyl, aryl, aralkyl, cycloalkyl, cycloalkylalkyl or lower alkenyl, with the proviso that when B is $-CH{=}CH-$, n is 1 to 3 or q is 1 to 4 and when B is a single bond, n is 1 to 5 or q is 1 to 6, and including all stereoisomers thereof.

The compounds are cardiovascular agents useful, for example, in the treatment of thrombolytic disease.

9 Claims, No Drawings

7-OXABICYCLOHEPTANE SUBSTITUTED PROSTAGLANDIN ALCOHOLS AND THEIR USE IN THE TREATMENT OF THROMBOLYTIC DISEASE

DESCRIPTION OF THE INVENTION

The present invention relates to 7-oxabicycloheptane substituted prostaglandin alcohols which are cardiovascular agents useful, for example, in the treatment of thrombolytic disease. These compounds have the structural formula

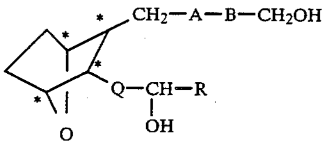

I and including all stereoisomers thereof, wherein A is $-CH=CH-(CH_2)_n-$ or $(CH_2)_q$; B is a single bond or $-CH=CH-$; n is 1 to 5; q is 1 to 6; Q is $-CH=CH-$ or $(CH_2)_2$; and R is lower alkyl, aryl, aralkyl, cycloalkyl, cycloalkylalkyl or lower alkenyl, with the proviso that when B is $-CH=CH-$, n is 1 to 3 or q is 1 to 4 and when B is a single bond, n is 1 to 5 or q is 1 to 6.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), and/or 1 or 2 lower alkoxy groups.

The term "aralkyl", "aryl-alkyl" or "aryl-lower alkyl" as used herein refers to lower alkyl groups as discussed above having an aryl substituent, such as benzyl or methylbenzyl

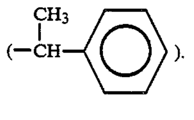

The term "lower alkenyl" or "alkenyl" includes straight or branched chain radicals of from 2 to 12 carbons, preferably 2 to 6 carbons in the normal chain, which include one double bond in the normal chain, such as ethenyl, 2-propenyl, 3-butenyl, 2-butenyl, 1-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkoxy", "alkoxy" or "aralkoxy" includes any of the above lower alkyl, alkyl or aralkyl groups linked to an oxygen atom.

The term "cycloalkylalkyl" as used herein refers to cycloalkyl groups as defined above linked to an alkyl group as defined above.

The term "lower alkoxy", "alkoxy" or "aralkoxy" includes any of the above lower alkyl, alkyl or aralkyl groups linked to an oxygen atom.

The terms "halogen" or "halo" as used herein refers to chlorine, bromine, fluorine or iodine with chlorine being preferred.

The terms "$(CH_2)_n$", "$(CH_2)_q$" and "$(CH_2)_2$" include straight or branched chain radicals having from 1 to 5 carbons in the normal chain in the case of $(CH_2)_n$, 1 to 6 carbons in the normal chain in the case of $(CH_2)_q$, and 2 carbons in the normal chain in the case of $(CH_2)_2$, and may contain one or more lower alkyl substituents. Examples of $(CH_2)_n$, $(CH_2)_q$ and $(CH_2)_2$ groups include

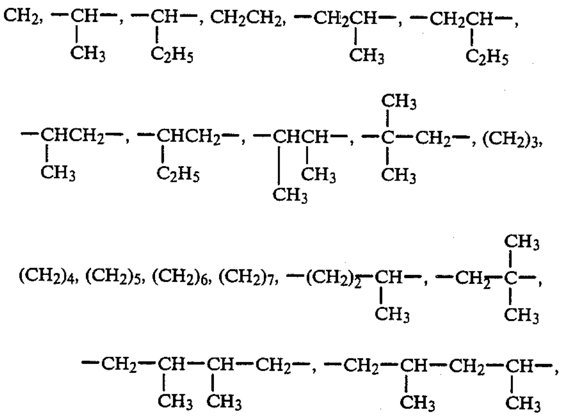

and the like.

Preferred are those compounds of formula I wherein A is $-CH=CH-(CH_2)_n-$, n is 2 or 3, B is a single bond, Q is CH=CH, and R is lower alkyl, aryl such as phenyl or aralkyl such as benzyl.

The various compounds of the invention may be prepared as described below.

The compounds of formula I of the invention (where B is a single bond) may be prepared as described below and according to the following reaction sequence.

A. Where A is $CH=CH-(CH_2)_n$ and B is a single bond

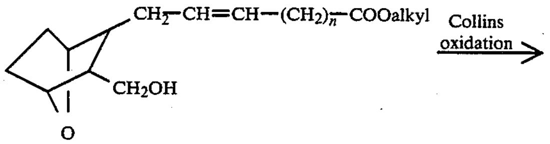

III

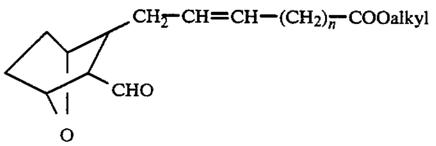

IV

-continued

B. Where A is $(CH_2)_q$ and B is a single bond

III 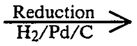

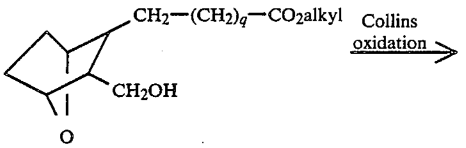

IIIA (where q = 2 + n)

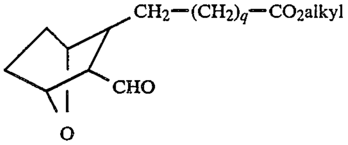

IVA

IV or IVA 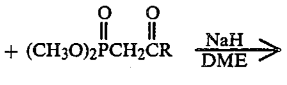

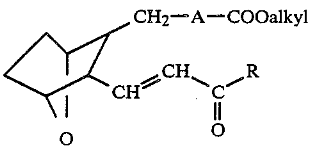

V (where A is $-CH{=}CH-(CH_2)_n-$ or $(CH_2)_q$)

V 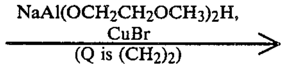

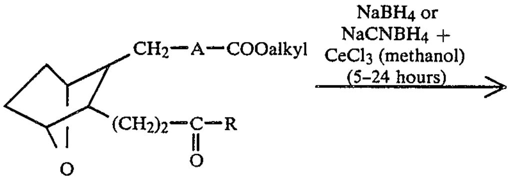

VA

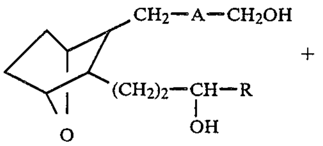

VI

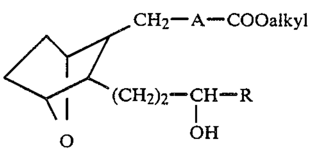

VIA

V 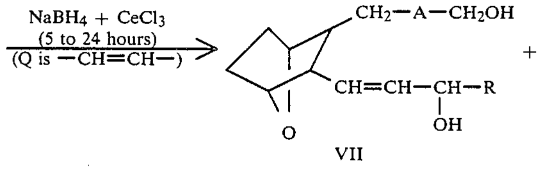

VII

-continued

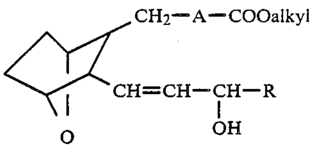

VIIA

The starting lower alkyl ester containing the hydroxymethyl group (that is, compound III where A is $CH{=}CH-(CH_2)_n$ or compound IIIA where A is $(CH_2)_q$ prepared as described in U.S. Pat. No. 4,143,054) is used to form the aldehyde IV or IVA, respectively. Thus, to form aldehyde IV, compound III is subjected to a Collins oxidation, for example, by reacting III with chromium oxide in pyridine. To form aldehyde IVA, compound III is first reduced by treatment with hydrogen in the presence of palladium on charcoal to form IIIA which is subjected to a Collins oxidation as described above to form aldehyde IVA.

Aldehyde IV or IVA of the structure

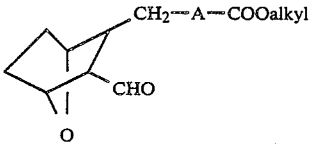

(IV where A is $CH{=}CH-(CH_2)_n$)

IVA where A is $(CH_2)_q$ with, q=2+n)

is reacted with a dialkoxy phosphonate, such as of the structure

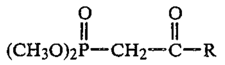

A employing a molar ratio of IV or IVA:A of within the range of from about 1:1 to about 0.5:1, under basic conditions, such as in the presence of sodium hydride or lithium diisopropylamide and an inert organic solvent, such as dimethoxyethane (DME), ether, tetrahydrofuran or toluene to form a compound of the structure

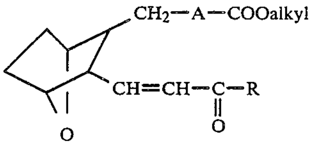

V

Compound V may then be reduced by two different ways as outlined above to form compounds VI or VII

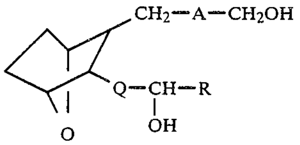

VI—Q is $(CH_2)_2$

VII—Q is $-CH{=}CH-$ or compounds of the general formula VIII

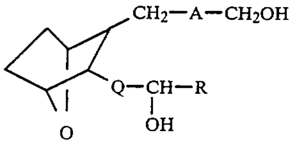

VIII

Thus, to form compound VI wherein Q is $(CH_2)_2$, compound V is first reacted with $NaAl(OCH_2CH_2OCH_3)_2H$ in the presence of CuBr and then the reaction product is reduced, for example, by treating with a reducing agent such as sodium borohydride or sodium cyanoborohydride in a solvent such as methanol and in the presence of cerium trichloride for a period of from about 5 to about 24 hours to form a mixture of compounds of formulae VI and VIA

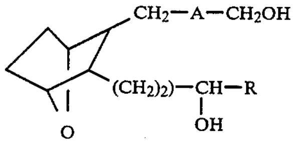

VI

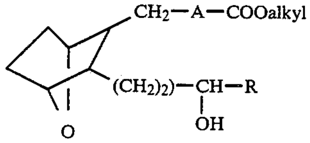

VIA

To form compound VII (where Q is CH═CH), ester V is reduced using sodium borohydride or sodium cyanoborohydride and cerium trichloride as described above to form a mixture of compounds of formulae VII and VIIA

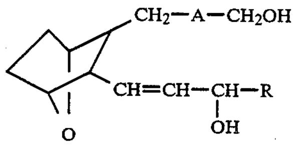

VII

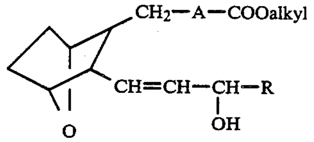

VIIA

Alcohols VIA and VIIA may be hydrolyzed by reaction with lithium hydroxide, potassium carbonate or sodium hydroxide in the presence of an inert organic solvent such as tetrahydrofuran, methanol or dimethoxyethane-water to form compounds of the invention VI and VII, respectively.

Compounds of the invention wherein B is —CH═CH—, that is,

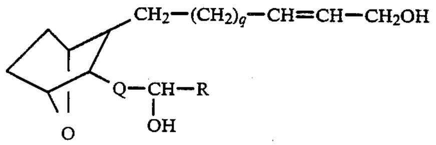

IX or

-continued

X

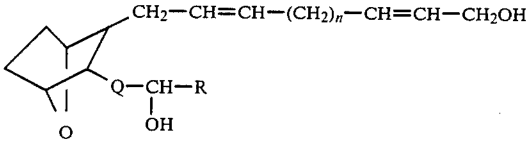

may be prepared as follows.

Compounds of formula IX may be prepared by subjecting the allylic alcohol VIII wherein A is $(CH_2)_q$, that is

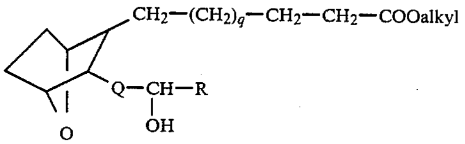

VIIIA or wherein A is CH═CH—$(CH_2)_n$, that is

VIIIB

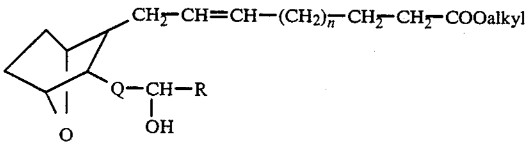

to tetrahydropyranyl ether formation by reacting allylic alcohol VIIIA with dihydropyran in the presence of an inert organic solvent such as methylene chloride or ether and catalytic amounts of p-toluene sulfonic acid at reduced temperatures of from about 0° C. to about 10° C., to form the tetrahydropyranyl ether of formula XI

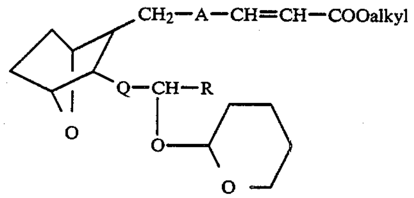

XI

The tetrahydropyranyl ether XI is then subjected to phenylselenylation by reacting XI with lithium diisopropylamide at reduced temperatures of from about −78° C. to about 0° C. in the presence of an inert organic solvent such as tetrahydrofuran or ether; thereafter a solution of diphenyl-diselenide in an inert organic solvent as described above is added and the reaction is maintained at reduced temperatures as described above to form the selenophenyl ester X

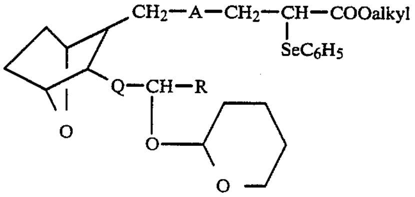

XI the selenophenyl ester XII is made to undergo a selenoxide elimination reaction wherein the selenophenyl ester XII in a cooled alcohol solvent and/or ethyl acetate is reacted with hydrogen peroxide at reduced temperatures of from about 0° C. to about 25° C., to form the unsaturated ester XI

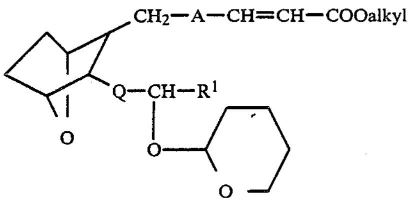

XIII which is then hydrolyzed by reaction with a strong acid such as HCl, Amberlyst Resin or acetic acid in the presence of dimethoxyethane, tetrahydrofuran or other inert solvent to form the ester XIV

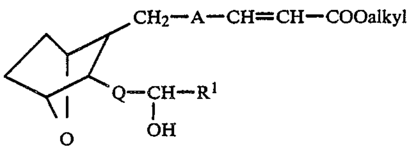

XIV

The ester XIV is then reduced by treatment with diisobutylaluminum hydride in an organic solvent such as ether, toluene or THF to form the alcohol IX or X.

The allylic alcohols VIIIA and VIIIB may be prepared by subjecting enone V or VA to a reduction step wherein VIIIA or VIIIB is treated with $NaBH_4$ or $NaCNBH_4$ and cerium trichloride in an organic solvent such as methanol for a period of from about 15 minutes to about 1.5 hours.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

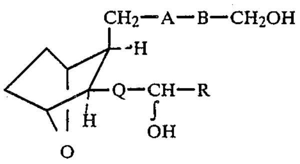

Ia (cis-endo)

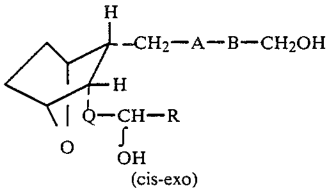

Ib (cis-exo)

-continued

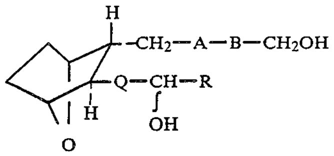

Ic (trans)

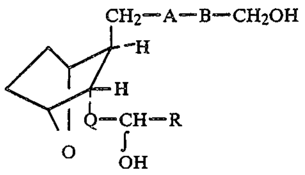

Id (trans)

The wavy line (∫) in the above formulae indicates that the hydroxy group in each of the compounds of formulae Ia–Id is either R(β) or S(α).

The nucleus in each of the compounds of the invention is depicted as

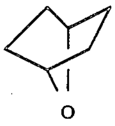

for matter of convenience; it will also be appreciated that the nucleus in the compounds of the invention may be depicted as

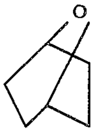

The compounds of this invention are cardiovascular agents useful as platelet aggregation inhibitors, such as inhibiting arachidonic acid-induced platelet aggregation (e.g., for treatment of thrombolytic disease, such as coronary or cerebral thromboses) and in inhibiting bronchoconstriction as induced by asthma. They are also selective thromboxane $A_2$ receptor antagonists and synthetase inhibitors, e.g., having a vasodilatory effect for treatment of myocardial ischemic disease, such as angina pectoris.

The compounds of the invention can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in degrees Centigrade.

EXAMPLE 1

1α,2β(Z),3β(1E,3R,4S),4α]-7-[3-(3-Hydroxy-4-phenyl-1-pentenyl)-7-oxabicyclo[2.2.1]hept-2-yl]-5-heptenol A. [1α,2β(Z),3β(1E),4α]-7-[3-(3-Oxo-4-phenyl-1-pentenyl)-7-oxabicyclo[2.2.1]hept-2-yl]-5-heptenoic acid, methyl ester (1) (+)-Methyl 2-phenylpropionate (+) 2-Phenylpropionic acid (8.4 g, 56 mmol) in methanol (180 ml) and concentrated $H_2SO_4$ (2 ml) were heated at reflux for 4 hours. The reaction was cooled down to room temperature and concentrated in vacuo (~100 ml). The products were extracted with $Et_2O$ (150 ml×3), which was washed with saturated $NaHCO_3$, $H_2O$ and dried over $MgSO_4$. Filtration and evaporation of solvent yielded a yellow oil (8.9 g), which was distilled to give (+) methyl 2-phenylpropionate as a colorless oil (8.34 g, 51 mmol, 91%, b.p. 73° C./1.5 mm Hg), $[\alpha]^D=+111°$ (c=2, toluene).

(2) (+)-2-Oxo-3-phenylbutyl dimethyl phosphonate n-Butyllithium (1.6M, 62.5 ml, 100 mmol) was added dropwise to a magnetically stirred solution of dimethylmethyl phosphonate (12.4 g, 100 mmol) in THF (90 ml) at −78° C. Stirring was continued for 30 minutes at −78° C. Then ester (8.2 g, 50 mmol) was added dropwise to give a yellow colored solution. After 3 hours stirring at −78° C., the reaction was warmed to room temperature and stirred for 1 hour. The reaction was quenched by addition of acetic acid to pH 5~6. The solvent was removed in vacuo and $H_2O$ (100 ml) was added. The products were extracted with $CH_2Cl_2$ (100 ml×3), which was washed with saturated $NaHCO_3$, $H_2O$ and dried over $MgSO_4$. Filtration and evaporation of solvent left a yellow oil. This was fractionated to give (+)2-oxo-3-phenylbutyl dimethyl phosphonate (8.1 g, 31.6 mmol, 63%, b.p. 142°-144° /0.2 mm Hg), $[\alpha]^D=+235°$ (c=2, toluene).

(3) [1α,2β(Z),3β(1E,4S)4α]-7-[3-(3-Oxo-4-phenyl-1-pentenyl)-7-oxabicyclo[2.2.1]hept-2-yl]-5-heptenoic acid, methyl ester Sodium hydride (201 mg of 50% in mineral oil, 4.18 mmol) was suspended in distilled dimethoxyethane (70 ml) in an argon atmosphere and treated with a solution of Part A(2) phosphonate (1.45 g, 4.7 mmol) in DME (10 ml). The mixture was stirred at room temperature 90 minutes. A solution of (+)[1α,2β(Z),3β,4α]-7-[3-formyl-7-oxabicyclo[2.2.1]hept-2-yl]-5-heptenoic acid, methyl ester (prepared as described in U.S. Pat. No. 4,143,054 by subjecting [1α,2β(Z),3β,4α]-7-[3-(hydroxymethyl)-7-oxabicyclo[2.2.1]hept-2-yl]-5-heptenoic acid, methyl ester to a Collins oxidation by reacting it with $CrO_3$ in pyridine) (1.031 g, 3.8 mmol) in DME (5 ml) was then added and the mixture was stirred overnight at room temperature. The reaction was quenched by adding glacial acetic acid (0.5 ml) and the solvent was removed in vacuo. Ether and saturated $NaHCO_3$ were added and the layers were separated. The ether layer was washed once with saturated $NaHCO_3$ solution, dried over $MgSO_4$, filtered and taken to dryness in vacuo leaving a viscous oil. This was chromatographed on silica gel 60 (110 g), eluting with ether-pet ether (2:3) to give 992 mg (66%) of title A (3) compound as an oil. A faster moving material (98 mg, 6.5%) was also isolated and identified by $^1H$ NMR as the cis double bond isomer.

B. [1α,2β(Z),3β(1E,3R,4S),4α]-7-[3-(3-Hydroxy-4-phenyl-1-pentenyl)-7-oxabicyclo[2.2.1]hept-2-yl]-5-heptenoic acid, methyl ester and [1α,2β(Z),3β(1E,3R,4S),4α]-7-[3-(3-Hydroxy-4-phenyl-1-pentenyl)-7-oxabicyclo[2.2.1]hept-2-yl]-5-heptenol To a solution of 1.2 g of title A (3) chiral enone (3 mmol) in 12 ml of dry methanol was added with stirring 1.2 g of ceric (111) chloride hydrate. After 5 minutes at room temperature, the homogeneous solution was cooled to −78° C. and 120 mg of solid sodium borohydride (~3 mmole) was added. The reaction mixture was left at −78° C. for 10 hours and was then gradually warmed to room temperature in ~14 hours. It was then quenched by addition of 1N aq. HCl solution and extracted with ether. The ether extract was dried over anhydrous magnesium sulfate and concentrated in vacuo to give 1.26 g of title crude oil.

C. [1α,2β(Z),3β(1E,3R,4S),4α]-7-[3-(3-Hydroxy-4-phenyl-1-pentenyl)-7-oxabicyclo[2.2.1]hept-2-yl]-5-heptenol To 1.6 g of Part B crude oil in 12 ml of distilled THF and 3 ml of water was added with stirring 4 ml of a 1N aqueous lithium hydroxide solution. After stirring at room temperature for 22 hours, an additional 2 ml of a 1N aqueous LiOH solution was added. The reaction mixture was stirred for an additional 3½ hours, whereupon it was acidified with 1N aqueous HCl solution and extracted with ether (×3). The combined ether extract was now extracted twice with saturated sodium bicarbonate solution to remove the acid. The ether extract was dried over anhydrous magnesium sulfate and concentrated in vacuo. The crude oily residue was chromatographed on a LPS-1 silica gel column and successively eluted with 20-50% ethyl acetate in hexane to obtain 275 mg of desired title chiral alcohol as a colorless oil.

Anal Calcd for $C_{24}H_{34}O_3$, 0.27M $H_2O$: C, 76.77; H, 9.27. Found: C, 76.71; H, 9.20.

EXAMPLE 2

[1α,2β(Z),3β(1E,3R),4α]-7-[3-(3-Hydroxy-3-phenyl-1-propenyl)-7-oxabicyclo[2.2.1]hept-2-yl]5-heptenol Following the procedure of Example 1 except substituting benzoic acid for 2-phenylpropionic acid, the title compound is obtained.

EXAMPLE 3

[1α,2β(Z),3β(1E,3R),4α]-7-[3-(3-Hydroxy-4-phenyl-1-butenyl)-7-oxabicyclo[2.2.1]hept-2-yl]5-heptenol Following the procedure of Example 1 except substituting phenylacetic acid for 2-phenylpropionic acid, the title compound is obtained.

EXAMPLE 4

[1α,2β(Z),3β(1E,3R),4α]-7-[3-(3-Hydroxy-3-cyclohexyl-1-propenyl)-7-oxabicyclo[2.2.1]hept-2-yl]-5-heptenol Following the procedure of Example 1 except substituting cyclohexyl carboxylic acid for 2-phenylpropionic acid, the title compound is obtained

EXAMPLE 5

[1α,2β(Z),3β(1E,3R),4α]-7-[3-(3-Hydroxy-4-cyclopentyl-1-butenyl)-7-oxabicyclo[2.2.1]hept-2-yl]-5-heptenol Following the procedure of Example 1 except substituting cyclopentylacetic acid for 2-phenylpropionic acid, the title compound is obtained.

EXAMPLE 6

[1α,2β(Z),3β(1E,3R),4α]-7-[3-(3-Hydroxy-1,5-hexadienyl)-7-oxabicyclo[2.2.1]hept-2-yl]-5-heptenol Following the procedure of Example 1 except substituting 2-propenyl carboxylic acid for 2-phenylpropionic acid, the title compound is obtained.

EXAMPLE 7

[1α,2β(Z),3β(1E,3R),4α]-7-[3-(3-Hydroxy-1-nonenyl)-7-oxabicyclo[2.2.1]hept-2-yl]-5-heptenol Following the procedure of Example 1 except substituting hexane carboxylic acid for 2-phenylpropionic acid, the title compound is obtained.

EXAMPLE 8

[1α,2β(Z),3β(1E,3R),4α]-7-[3-(3-Hydroxy-1-pentenyl)-7-oxabicyclo[2.2.1]hept-2-yl]-5-heptenol Following the procedure of Example 1 except substituting propionic acid for 2-phenylpropionic acid, the title compound is obtained.

EXAMPLE 9

[1S-[1α,2β(Z),3β(4S),4α]-7-[3-(3-Hydroxy-4-phenyl-1-pentyl)-7-oxabicyclo2.2.1]hept-2-yl]-5-heptenol

A.

[1S-[1α,2β(Z),3β(4S),4α]]-7-[3-(3-Oxo-4-phenyl-1-pentyl)-7-oxabicyclo[2.2.1]hept-2-yl]-5-heptenoic acid, methyl ester To a suspension of 686 mg of purified cuprous bromide (4.8 mmole) in 12 ml of dry THF, cooled at 0°-5° C. was added with stirring 1.35 ml of a 3.5M solution of red-Al (sodium bis(2-methoxyethoxy)aluminumhydride) in toluene dropwise. The solution was stirred at 0°-5° C. for 30 minutes, whereupon it was cooled to −78° C. and 2 ml of n-butanol (18 mmole) was added rapidly, followed by a solution of 476 mg of Example 1 Part A (3) enone (1.2 mmole) in 4 ml of dry THF. After 10 minutes at −78° C., the reaction mixture was warmed to −20° C. and left for an additional one hour. The reaction mixture was quenched by addition of 70 ml of water and then poured into saturated ammonium chloride solution and was extracted with ether (×3). The ether extract was dried over anhydrous magnesium sulfate, filtered and the filtrate was concentrated under reduced pressure. 480 mg of desired title ketone was obtained (100% yield) as a colorless oil.

B.

[1S-[1α,2β(Z),3β(4S),4α]-7-[3-(3-Hydroxy-4-phenyl-1-pentyl)-7-oxabicyclo[2.2.1]hept-2-yl]-5-heptenol Following the procedure of Example 1 except substituting the Part A enone for the Example 1 Part A (3) enone, the title compound is obtained.

EXAMPLE 10

[1α,2β(Z),3β,4α]-7-[3-(3-Hydroxy-3-phenyl-1-propyl)-7-oxabicyclo[2.2.1]hept-2-yl]-5-heptenol Following the procedure of Example 9 and Example 1 except substituting benzoic acid for 2-phenylpropionic acid, the title compound is obtained.

EXAMPLE 11

[1α,2β(E),3β,4α]-7-[3-(3-Hydroxy-4-phenyl-1-butyl)-7-oxabicyclo[2.2.1]hept-2-yl]-5-heptenol Following the procedure of Example 9 and Example 1 except substituting phenylacetic acid for 2-phenylpropionic acid, the title compound is obtained.

EXAMPLE 12

[1α,2β(Z),3β,4α]-7-[3-(3-Hydroxy-3-cyclohexyl-1-propyl)-7-oxabicyclo[2.2.1]hept-2-yl]-5-heptenol Following the procedure of Example 16 and Example 1 except substituting cyclohexylcarboxylic acid for 2-phenylpropionic acid, the title compound is obtained.

EXAMPLE 13

[1α,2β(Z),3β,4α]-7-[3-(3-Hydroxy-4-cyclopentyl-1-butyl)-7-oxabicyclo[2.2.1]hept-2-yl]-5-heptenol Following the procedure of Example 9 and Example 1 except substituting cyclopentylacetic acid for 2-phenylpropionic acid, the title compound is obtained.

EXAMPLE 14

[1α,2β(Z),3β,4α]-7-[3-(3-Hydroxy-5-hexenyl)-7-oxabicyclo[2.2.1]hept-2-yl]-5-heptenol Following the procedure of Example 9 and Example 1 except substituting 2-propenyl carboxylic acid for 2-phenylpropionic acid, the title compound is obtained.

EXAMPLE 15

[b

1α,2β(Z),3β,4α]-7-[3-(3-Hydroxy-1-nonyl)-7-oxabicyclo[2.2.1]hept-2-yl]-5-heptenol Following the procedure of Example 9 and Example 1 except substituting hexanecarboxylic acid for 2-phenylpropionic acid, the title compound is obtained.

EXAMPLE 16

[1α,2β,3β(4S),4α]-7-[3-(3-Hydroxy-4-phenyl-1-pentenyl)-7-oxabicyclo[2.2.1]hept-2-yl]heptanol A. (1α,2β,3β,4α)-7-[3-(Hydroxymethyl)-7-oxabicyclo[2.2.1]hept-2-yl]heptanoic acid, methyl ester To 800 mg (3.0 mmole) of the [1α,2β(Z),3β,4α]-7-[3-(hydroxymethyl)-7-oxabicyclo[2.2.1]hept-2-yl]-5-heptenoic acid, methyl ester dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.

[1α,2β,3β(4S),4α]-7-[3-(3-Hydroxy-4-phenyl-1-pentenyl)-7-oxabicyclo[2.2.1]hept-2-yl]-5-heptanol Following the procedure of Example 1 except substituting the Part A alcohol-ester for the alcohol ester used in Example 1A (3), the title product is obtained.

EXAMPLE 17

(1α,2β,3β,4α)-7-[3-(3-Hydroxy-3-phenyl-1-propenyl)-7-oxabicyclo[2.2.1]hept-2-yl]heptanol Following the procedure of Example 16 and Example 1 except substituting benzoic acid for 2-phenylpropionic acid, the title compound is obtained.

EXAMPLE 18

(1α,2β,3β,4α)-7-[3-(3-Hydroxy-4-phenyl-1-butenyl)-7-oxabicyclo2.2.1]hept-2-yl]heptanol Following the procedure of Example 16 and Example 1 except substituting phenylacetic acid for 2-phenylpropionic acid, the title compound is obtained.

EXAMPLE 19

1α,2β,

3β,4α)-7-[3-(3-Hydroxy-3-cycloheptyl-1-propenyl)-7-oxabicyclo[2.2.1]hept-2-yl]heptanol Following the procedure of Example 16 and Example 1 except substituting cycloheptyl acid for 2-phenylpropionic acid, the title compound is obtained.

EXAMPLE 20

(1α,2β,3β,4α)-7-[3-(3-Hydroxy-4-cyclohexyl-1-butenyl)-7-oxabicyclo[2.2.1]hept-2-yl]heptanol Following the procedure of Example 16 and Example 1 except substituting cyclohexylacetic acid for 2-phenylpropionic acid, the title compound is obtained.

EXAMPLE 21

(1α,2β,3β,4α)-7-[3-(3-Hydroxy-1,5-hexadienyl)-oxabicyclo[2.2.1]hept-2-yl]heptanol Following the procedure of Example 16 and Example 1 except substituting 2-propenyl carboxylic acid for 2-phenylpropionic acid, the title compound is obtained.

EXAMPLE 22

(1α,2β,3β,4α)-7-[3-(3-Hydroxy-1-nonenyl)-7-oxabicyclo[2.2.1]hept-2-yl]heptanol

Following the procedure of Example 16 and Example 1 except substituting hexane carboxylic acid for 2-phenylpropionic acid, the title compound is obtained.

EXAMPLE 23

(1α,2β,3β,4α)-7-[3-(3-Hydroxy-1-pentenyl)-7-oxabicyclo2.2.1]hept-2-yl]heptanol

Following the procedure of Example 16 and Example 1 except substituting propionic acid for -phenylpropionic acid, the title compound is obtained.

EXAMPLE 24

(1α,2β,3β,4α)-7-[3-(3-Hydroxy-4-phenyl-1-pentyl)-oxabicyclo[2.2.1]hept-2-yl]heptanol

A.

(1α,2β,3β,4α)-7-[3-(Hydroxymethyl)-7-oxabicyclo[2.2.1]hept-2-yl]-heptanoic acid, methyl ester To 800 mg (3.0 mmole) of the [1α,2β(Z),-3β,4α]-7-[3-(hydroxymethyl)-7-oxabicyclo[2.2.1]-hept-2-yl]-5-heptenoic acid, methyl ester dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B. [1α,2β,3β(4S,4α]-7-[3-(3-Oxo-4-phenyl-1-pentenyl)-7-oxabicyclo[2.2.1]hept-2-yl]heptanol Following the procedure of Example 1 Parts A (1) to A (3) except substituting the Part A alcohol-ester for the alcohol ester used in Example 1A (3), the title enone is obtained.

C.

[1α,2β,3β(4S),4α]-7-[3-(3-Oxo-4-phenyl-1-pentyl)-7-oxabicyclo[2.2.1]-hept-2-yl]heptanol To a suspension of 686 mg of purified cuprous bromide (4.8 mmole) in 12 ml of dry THF, cooled at 0°-5° C. is added with stirring 1.35 ml of a 3.5 M solution of red-Al (sodium bis(2-methoxyethoxy)aluminumhydride) in toluene dropwise. The solution is stirred at 0°-5° C. for 30 minutes, whereupon it is cooled to −78° C. and 2 ml of n-butanol (18 mmole) is added rapidly, followed by a solution of 476 mg of the title B enone (1.2 mmole) in 4 ml of dry THF. After 10 minutes at −78° C., the reaction mixture is warmed to −20° C. and left for an additional one hour. The reaction mixture is quenched by addition of 70 ml of water and then poured into saturated ammonium chloride solution and was extracted with ether (×3). The ether extract is dried over anhydrous magnesium sulfate, filtered and the filtrate is concentrated under reduced pressure. 478 mg of desired title ketone is obtained (100% yield) as a colorless oil.

D.

[1α,2β,3β(4S),4α]-7-[3-(3-Hydroxy-4-phenyl-1-pentyl)-7-oxabicyclo[2.2.1]hept-2-yl]heptanol Following the procedure of Example 1 except substituting the above title C enone for the Example 1 Part A (3) enone, the title compound is obtained.

EXAMPLE 25

(1α,2β,3β,4α)-7-[3-(3-Hydroxy-3-phenyl-1-propyl)-7-oxabicyclo[2.2.1]hept-2-yl]heptanol Following the procedure of Example 24 except substituting benzoic acid for 2-phenylpropionic acid, the title compound is obtained.

EXAMPLE 26

(1α,2β,3β,4α)-7-[3-(3-Hydroxy-4-phenyl-1-butyl)--oxabicyclo[2.2.1]hept-2-yl]heptanol Following the procedure of Example 24 except substituting phenylacetic acid for 2-phenylpropionic acid, the title compound is obtained.

EXAMPLE 27

(1α,2β,3β,4α)-7-[3-(3-Hydroxy-3-cyclohexyl-1-propyl)-7-oxabicyclo[2.2.1]hept-2-yl]heptanol Following the procedure of Example 24 except substituting cyclohexyl carboxylic acid for 2-phenylpropionic acid, the title compound is obtained.

EXAMPLE 28

(1α,2β,3β,4α)-7-[3-(3-Hydroxy-4-cyclopentyl-1-butyl)-7-oxabicyclo-2.2.1]hept-2-yl]heptanol Following the procedure of Example 24 except substituting cyclopentyl carboxylic acid for 2-phenylpropionic acid, the title compound is obtained.

EXAMPLE 29

(1α,2β,3β,4α)-7-[3-(3-Hydroxy-5-hexenyl)-7-oxabicyclo[2.2.1hept-2-yl]heptanol

Following the procedure of Example 24 except substituting 2-propenyl carboxylic acid for 2-phenylpropionic acid, the title compound is obtained.

EXAMPLE 30

(1α,2β,3β,4α)-7-[3-(3-Hydroxy-1-octyl)-7-oxabicyclo[2.2.1]hept-2-yl]heptanol

Following the procedure of Example 24 except substituting pentane carboxylic acid for 2-phenylpropionic acid, the title compound is obtained.

EXAMPLE 31

[1α,2β(2E,5Z),3β(1E,3R,4S),4α]-7-[3-(3-Hydroxy-4-phenyl-1-pentenyl)-7-oxabicyclo[2.2.1]hept-2-yl]-2,5-heptadienol

A.

[1α,2β(Z),3β(1E,4S)]-7-[3-(3-Tetrahydropyranyloxy-4-phenyl-1-pentenyl)-7-oxabicyclo[2.2.1]hept-2-yl]-2,5-heptenoic acid, methyl ester To a solution of 2.16 g of Example 1 title B allylic alcohol (5.4 mmole) in 20 ml of dry methylene chloride is added with stirring a catalytic amount of p-toluene sulfonic acid, followed by 750 μl of dihydropyran (8.33 mmole) at 0°-5° C. The reaction mixture was stirred at 0°-5° C. for 40 minutes whereupon it was washed with aqueous sodium bicarbonate solution. The methylene chloride layer was separated and the aqueous layer was extracted with ether. The combined organic extract was dried over anhydrous magnesium sulfate and concentrated under reduced pressure. Purification by flash chromatography on a silica gel column gave 2.43 g of desired title THP-ether (eluting solvent 10-15% ethyl acetate in hexane).

B.

[1α,2β(Z),3β(1E,3R,4S),4α]-7-[3-(3-Tetrahydropyranyloxy-4-phenyl-1-pentenyl)-7-oxabicyclo[2.2.1]hept-2-yl]-2-selenophenyl-5-heptenoic acid, methyl ester To a solution of 2 ml of distilled diisopropylamine (13 mmole, distilled over $CaH_2$) in 30 ml of dry THF, cooled at −78° C. in a dry ice-acetone bath was added dropwise 7.5 ml of a 1.6 M solution of n-butyllithium in hexane (12 mmole). The solution of lithium diisopropylamide so formed was stirred at −78° C. for 30 minutes, whereupon a solution of 2.43 g of title B THP-ether (5 mmole) in 15 ml of dry THF was added dropwise over a period of 10 minutes. The colorless solution was stirred at −78° C. for an additional 30 minutes, whereupon a solution of 3.75 g of diphenyl-diselenide (12 mmole) in 5 ml of dry THF was added dropwise. Initially the yellow color of diselenide discharged immediately upon addition. The yellow solution was stirred at −78° C. for 30 minutes, whereupon the cooling bath was removed. After 30 minutes the reaction mixture was quenched by addition of aqueous ammonium chloride solution. It was then diluted with water and the organic layer was separated. The aqueous layer was extracted with ether. The combined organic extract was dried over anhydrous magnesium sulfate and concentrated under reduced pressure. The crude residue was chromatographed on a silica gel column. Elution with 5-15% ethyl acetate in hexane gave 2.6 g of title α-selenophenyl ester as a colorless oil.

C.

[1α,2β(2E,5Z),3β(1E,3R,4S),4α]-7-[3-(3-Tetrahydropyranyloxy-4-phenyl-1-pentenyl)-7-oxabicyclo[2.2.1]hept-2-yl]-2,5-heptadienoic acid, methyl ester To a solution of 600 mg of title B seleno ester (0.94 mmole) in 6 ml of ethyl acetate and 4 ml of methanol, cooled in an ice-water bath was added with stirring 1 ml of a 30% aqueous hydrogen peroxide solution. After 30 minutes at 0°-5° C., the reaction mixture was warmed to room temperature and stirred for an additional one hour. The reaction mixture was diluted with ether and washed with water. The organic layer was dried over anhydrous magnesium sulfate and concentrated under reduced pressure. The crude residue was chromatographed on a silica gel column and eluted with 10-20% ethyl acetate in hexane to obtain 320 mg of title α,β-unsaturated ester.

D.

[[1α,2β(2E,5Z),3β(1E,3R,4S),4α]-7-[3-(3-Hydroxy-4-phenyl-1-pentenyl)-7-oxabicyclo[2.2.1]hept-2-yl]-2,5-heptadienoic acid, methyl ester To a solution of 320 mg of title C α,β-unsaturated ester in 10 ml of distilled dimethoxyethane (DME) was added with stirring 3 ml of a 2N aqueous hydrochloric acid solution. The reaction mixture was stirred under an argon atmosphere for 24 hours, whereupon it was diluted with ether and washed with water. The organic extract was dried over anhydrous magnesium sulfate and concentrated under reduced pressure. The crude residue was chromatographed on a silica gel column and eluted with 20-30% ethyl acetate in hexane to obtain 245 mg of title methyl ester.

E.

[1α,2β(2E,5Z),3β(1E,3R,4S),4α]-7-[3-(3-Hydroxy-4-phenyl-1-pentenyl)-7-oxabicyclo[2.2.1]hept-2-yl]-2,5-heptadienol To a solution of 245 mg of title D unsaturated ester (0.616 mmole) in 10 ml of dry THF is added with stirring at −78° C., 2 ml of a 1.76 M solution of di-isobutyl aluminum hydride in toluene. After 3 hours at −78° C., excess hydride reagent is destroyed by addition of aqueous ammonium chloride solution. The reaction mixture is diluted with ether and washed with 1N aqueous hydrochloric acid solution, water, and saturated salt solution. The organic extract is dried over anhydrous magnesium sulfate and concentrated under reduced pressure to obtain the above title dienol.

EXAMPLE 32

[1α,2β(2E,5Z),3β(1E,3R,4S),4α]-7-[3-(3-Hydroxy-3-phenyl-1-propenyl)-7-oxabicyclo[2.2.1]hept-2-yl]-2,5-heptadienol Following the procedure of Example 31 and Example 1 except substituting in Example 1 benzoic acid for 2-phenylpropionic acid, the title compound is obtained.

EXAMPLE 33

[1α,2β(2E,5Z),3β(1E,3R),4α]-7-[3-(3-Hydroxy-4-phenyl-1-butenyl)-7-oxabicyclo[2.2.1]hept-2-yl]-2,5-heptadienol Following the procedure of Example 31 and Example 1 except substituting in Example 1 phenylacetic acid for 2-phenylpropionic acid, the title compound is obtained.

EXAMPLE 34

[1α,2β(2E,5Z),3β(1E,3R),4α]-7-[3-(3-Hydroxy-3-cyclopentyl-1-propenyl)-7-oxabicyclo[2.2.1]hept-2-yl]-2,5-heptadienol Following the procedure of Example 31 and Example 1 except substituting in Example 1 cyclopentyl carboxylic acid for 2-phenylpropionic acid, the title compound is obtained.

EXAMPLE 35

[1α,2β(2E,5Z),3β(1E,3R),4α]-7-[3-(3-Hydroxy-4-cyclohexyl-1-butenyl)-7-oxabicyclo[2.2.1]-hept-2-yl]-2,5-heptadienol Following the procedure of Example 31 and Example 1 except substituting in Example 1 cyclohexylacetic acid for 2-phenylpropionic acid, the title compound is obtained.

EXAMPLE 36

[1α,2β(2E,5Z),3β(1E,3R),4α]-7-[3-(3-Hydroxy-1,4-heptadienyl)-7-oxabicyclo[2.2.1]hept-2-yl]-2,5-heptadienol Following the procedure of Example 31 and Example 1 except substituting in Example 1 3-butenyl carboxylic acid for 2-phenylpropionic acid, the title compound is obtained.

EXAMPLE 37

[1α,2β(2E,5Z),3β(1E,3R),4α]-7-[3-(3-Hydroxy-1-nonenyl)-7-oxabicyclo[2.2.1]hept-2-yl]-2,5-heptadienol Following the procedure of Example 31 and Example 1 except substituting in Example 1 hexane carboxylic acid for 2-phenylpropionic acid, the title compound is obtained.

EXAMPLE 38

[1α,2β(2E,5Z),3β(1E,3R),4α]-7-[3-(3-Hydroxy-1-pentenyl)-7-oxabicyclo[2.2.1]hept-2-yl]-2,5-heptadienol Following the procedure of Example 31 and Example 1 except substituting in Example 1 propionic acid for 2-phenylpropionic acid, the title compound is obtained.

EXAMPLE 39

[1α,2β(2E,5Z),3β(3R,4S),4α]-7-[3-(3-Hydroxy-4-phenyl-1-pentyl)-7-oxabicyclo[2.2.1]hept-2-yl]-2,5-heptadienol

A.

[1S-[1α,2β(Z),3β(4S),4α]]-7-[3-(3-Oxo-4-phenyl-1-pentyl)-7-oxabicyclo[2.2.1]hept-2-yl]-5-heptenoic acid, methyl ester To a suspension of 686 mg of purified cuprous bromide (4.8 mmole) in 12 ml of dry THF, cooled at 0°-5° C. was added with stirring 1.35 ml of a 3.5 M solution of red-Al (sodium bis(2-methoxyethoxy)aluminumhydride) in toluene dropwise. The solution was stirred at 0°-5° C. for 30 minutes, whereupon it was cooled to −78° C. and 2 ml of n-butanol (18 mmole) was added rapidly, followed by a solution of 476 mg of Example 1 Part A (3) enone (1.2 mmole) in 4 ml of dry THF. After 10 minutes at −78° C., the reaction mixture was warmed to −20° C. at −78° C., and left for an additional one hour. The reaction mixture was quenched by addition of 70 ml of water and then poured into saturated ammonium chloride solution and was extracted with ether (×3). The ether extract was dried over anhydrous magnesium sulfate, filtered and the filtrate was concentrated under reduced pressure. 480 mg of desired title ketone was obtained (100% yield) as a colorless oil.

B.

[1S-[1α,2β(Z),3β(3R,4S),4α]]-7-[3-(3-Hydroxy-4-phenyl-1-pentyl)-7-oxabicyclo-[2.2.1]hept-2-yl]-5-heptenoic acid, methyl ester To a solution of 400 mg of title A ketone (1 mmole) in 2 ml of methanol and 2 ml of dry THF is added with stirring 400 mg of ceric (III) chloride hydrate (1 mmole). After stirring at room temperature for 10 minutes, the reaction mixture is cooled to −50° C. and 40 mg of solid sodium borohydride (~1 mmole) is added to the reaction mixture. The reaction mixture is stirred at −50° C. for 45 minutes, whereupon 5 ml of acetone is added to destroy excess of borohydride. The mixture is stirred for an additional 5 minutes at −50° C . The cooling bath is removed and the reaction mixture is evaporated to dryness. The crude residue is diluted with ether and washed with 1N aqueous solution. The ether extract is dried over anhydrous $MgSO_4$ and concentrated under reduced pressure. The crude residue is chromatographed on a silica gel column and eluted with 30-50% ethyl acetate in hexane to obtain the desired title 3R-alcohol.

C.

[1S-[1α,2β(2E,5Z),3β(3R,4S)]-7-[3-(3-Hydroxy-4-phenyl-1-pentyl)-7-oxabicyclo[2.2.1]hept-2-yl]-2,5-heptadienol Following the procedure of Example 31 except substituting the Part B allylic alcohol for the Example 1 Part B alcohol, the title compound is obtained.

EXAMPLE 40

[1α,2β(2E,5Z),3β(1E,3R),4α]-7-3-(3-Hydroxy-3-phenyl-1-propyl)-7-oxabicyclo[2.2.1]hept-2-yl]-2,5-heptadienol Following the procedure of Example 39 and Example 1 Part A except substituting benzoic acid for 2-phenylpropionic acid in Example 1 Part A (1), the title compound is obtained.

EXAMPLE 41

[1α,2β(2E,5Z),3β(1E,3R),4α]-7-[3-(3-Hydroxy-4-phenyl-1-butyl)-7-oxabicyclo[2.2.1]hept-2-yl]-2,5-heptadienol Following the procedure of Example 39 and Example 1 Part A except substituting phenylacetic acid for 2-phenylpropionic acid in Example 1 Part A (1), the title compound is obtained.

EXAMPLE 42

[1α,2β(2E,5Z),3β(1E,3R),4α]-7-[3-(3-Hydroxy-3-cyclopentyl-1-propyl)-7-oxabicyclo[2.2.1]hept-2-yl]-2,5-heptadienol Following the procedure of Example 39 and Example 1 Part A except substituting cyclopentyl carboxylic acid for 2-phenylpropionic acid in Example 1 Part A (1), the title compound is obtained.

EXAMPLE 43

[1α,2β(2E,5Z),3β(1E,3R),4α]-7-[3-(3-Hydroxy-4-cyclohexyl-1-butyl)-7-oxabicyclo[2.2.1]hept-2-yl]-2,5-heptadienol Following the procedure of Example 39 and Example 1 Part A except substituting cyclohexylacetic acid for 2-phenylpropionic acid in Example 1 Part A (1), the title compound is obtained.

EXAMPLE 44

[1α,2β(2E,5Z),3β(1E,3R),4α]-7-[3-(3-Hydroxy-5-hexenyl)-7-oxabicyclo[2.2.1]hept-2-yl]-2,5-heptadienol Following the procedure of Example 39 and Example 1 Part A except substituting 2-propenyl carboxylic acid for 2-phenylpropionic acid in Example 1 Part A (1), the title compound is obtained.

EXAMPLE 45

[1α,2β(2E,5Z),3β(1E,3R),4α]-7-[3-(3-Hydroxy-1-nonyl)-7-oxabicyclo[2.2.1]hept-2-yl]-2,5-heptadienol Following the procedure of Example 39 and Example 1 Part A except substituting hexane carboxylic acid for 2-phenylpropionic acid in Example 1 Part A (1), the title compound is obtained.

EXAMPLE 46

(1α,2β,3β,4α)-7-[3-(3-Hydroxy-4-phenyl-1-pentenyl)-7-oxabicyclo[2.2.1]hept-2-yl]-2-heptenol

A.

(1α,2β,3β,4α)-7-[3-(Hydroxymethyl)-7-oxabicyclo[2.2.1]hept-2-yl]-heptanoic acid, methyl ester To 800 mg (3.0 mmole) of the [1α,2β(Z),-3β,4α]-7-[3-(hydroxymethyl)-7-oxabicyclo[2.2.1]hept-2-yl]-5-heptenoic acid, methyl ester dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.

(1α,2β,3β,4α)-7-[3-(3-Hydroxy-4-phenyl-1-pentenyl)-7-oxabicyclo[2.2.1]hept-2-yl]heptanoic acid, methyl ester Following the procedure of Example 1 Parts A and B except substituting the Part A alcohol-ester for the alcohol ester used in Example 1A (3), the title compound is obtained.

C.

(1α,2β,3β,4α)-7-[3-(3-Hydroxy-4-phenyl-1-pentenyl)-7-oxabicyclo[2.2.1]hept-2-yl]-2-heptenol Following the procedure of Example 31 except substituting the above title B alcohol for the Example 1 title B alcohol, the title compound is obtained.

EXAMPLE 47

(1α,2β,3β,4α)-7-[3-(3-Hydroxy-3-phenyl-1-pentenyl)-7-oxabicyclo[2.2.1]hept-2-yl-2-heptenol Following the procedure of Examples 46, 31 and Example 1 Parts A and B except substituting benzoic acid for 2-phenylpropionic acid in Example 1 Part A (1), the title compound is obtained.

EXAMPLE 48

(1β,2β,3β,4α)-7-[3-(3-Hydroxy-4-phenyl-1-butenyl)-7-oxabicyclo[2.2.1]hept-2-yl]-2-heptenol Following the procedure of Examples 46, 31 and Example 1 Parts A and B except substituting phenylacetic acid for 2-phenylpropionic acid in Example 1 Part A (1), the title compound is obtained.

EXAMPLE 49

(1α,2β,3β,4α)-7-[3-(3-Hydroxy-3-cyclohexyl-1-propenyl)-7-oxabicyclo[2.2.1]hept-2-yl]-2-heptenol Following the procedure of Examples 46, 31 and Example 1 Parts A and B except substituting cyclohexyl carboxylic acid for 2-phenylpropionic acid in Example 1 Part A (1), the title compound is obtained.

EXAMPLE 50

(1α,2β,3β,4α)-7-[3-(3-Hydroxy-4-cyclopentyl-1-butenyl)-7-oxabicyclo[2.2.1]hept-2-yl]-2-heptenol Following the procedure of Examples 46, 31 and Example 1 Parts A and B except substituting cyclopentylacetic acid for 2-phenylpropionic acid in Example 1 Part A (1), the title compound is obtained.

EXAMPLE 51

(1α,2β,3β,4α)-7-[3-(3-Hydroxy-1,5-hexdienyl)-7-oxabicyclo2.2.1]hept-2-yl]-2-heptenol Following the procedure of Examples 46, 31 and Example 1 Parts A and B except substituting 2-propenylcarboxylic acid for 2-phenylpropionic acid in Example 1 Part A (1), the title compound is obtained.

EXAMPLE 52

(1α,2β,3β,4α)-7-[3-(3-Hydroxy-4-phenyl-1-pentyl)-7-oxabicyclo[2.2.1]hept-2-yl]-2-heptenol

A.

(1α,2β,3β,4α)-7-3-(Hydroxymethyl)-7-oxabicyclo[2.2.1]hept-2-yl]heptanoic acid, methyl ester To 800 mg (3.0 mmole) of the [1α,2β(Z),-3β,4α]-7-[3-(hydroxymethyl)-7-oxabicyclo[2.2.1]-hept-2-yl]-5-heptenoic acid, methyl ester dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.

(1α,2β,3β,4α)-7-[3-(3-Oxo-4-phenyl-1-pentenyl)-7-oxabicyclo[2.2.1]hept-2-yl]heptanol Following the procedure of Example 1 Parts A (1) to A (3) except substituting the Part A alcohol-ester for the alcohol ester used in Example 1A (3), the title enone is obtained.

C.

(1α,2β,3β,4α)-7-[3-(3-Oxo-4-phenyl-1-pentyl)-7-oxabicyclo[2.2.1]hept-2-yl]-heptanol To a suspension of 686 mg of purified cuprous bromide (4.8 mmole) in 12 ml of dry THF, cooled at 0°-5° C. is added with stirring 1.35 ml of a 3.5 M solution of red-Al (sodium bis(2-methoxyethoxy)aluminumhydride) in toluene dropwise. The solution is stirred at 0°-5° C. for 30 minutes, whereupon it is cooled to −78° C. and 2 ml of n-butanol (18 mmole) is added rapidly, followed by a solution of 476 mg of the title B enone (1.2 mmole) in 4 ml of dry THF. After 10 minutes at −78° C., the reaction mixture is warmed to −20° C. and left for an additional one hour. The reaction mixture is quenched by addition of 70 ml of water and then poured into saturated ammonium chloride solution and was extracted with ether (×3). The ether extract was dried over anhydrous magnesium sulfate, filtered and the filtrate is concentrated under reduced pressure. 480 mg of desired title ketone was obtained (100% yield) as a colorless oil.

D.

[1S-[1α,2β(Z),3β(3R,4S),4α]]-7-[3-(3-Hydroxy-4-phenyl-1-pentyl)-7-oxabicyclo-[2.2.1]hept-2-yl]heptanoic acid, methyl ester To a solution of 400 mg of title C ketone (1 mmole) in 2 ml of methanol and 2 ml of dry THF is added with stirring 400 mg of ceric (III) chloride hydrate (1 mmole). After stirring at room temperature for 10 minutes, the reaction mixture is cooled to −50° C. and 40 mg of solid sodium borohydride (~1 mmole) is added to the reaction mixture. The reaction mixture is stirred at −50° C. for 45 minutes, whereupon 5 ml of acetone is added to destroy excess of borohydride. The mixture is stirred for an additional 5 minutes at −50° C. The cooling bath is removed and the reaction mixture is evaporated to dryness. The crude residue is diluted with ether and washed with 1N aqueous

E.

(1α,2β,3β,4α)-7-[3-(3-Hydroxy-4-phenyl-1-pentyl)-7-oxabicyclo[2.2.1]hept-2-yl]-2-heptenol Following the procedure of Example 31 except substituting the above title D alcohol for the Example 1 Part B alcohol, the title compound is obtained.

EXAMPLE 53

(1α,2β,3β,4α)-7-[3-(3-Hydroxy-3-phenyl-1-propyl)-7-oxabicyclo[2.2.1]hept-2-yl]-2-heptenol Following the procedure of Example 52 and 31 and Example 1 Parts A and B except substituting benzoic acid for 2-phenylpropionic acid in Example 1 Part A (1), the title compound is obtained.

EXAMPLE 54

(1α,2β,3β,4α)-7-[3-(3-Hydroxy-4-phenyl-1-butyl)-7-oxabicyclo[2.2.1]hept-2-yl]-2-heptenol Following the procedure of Example 52 and 31 and Example 1 Parts A and B except substituting phenylacetic acid for 2-phenylpropionic acid in Example 1 Part A (1), the title compound is obtained.

EXAMPLE 55

(1α,2β,3β,4α)-7-[3-(3-Hydroxy-3-cyclohexyl-1-propyl)-7-oxabicyclo[2.2.1]hept-2-yl]-2-heptenol Following the procedure of Example 52 and 31 and Example 1 Parts A and B except substituting cyclohexyl carboxylic acid for 2-phenylpropionic acid in Example 1 Part A (1), the title compound is obtained.

EXAMPLE 56

(1α,2β,3β,4α)-7-[3-(3-Hydroxy-3-cyclopentyl-1-butyl)-7-oxabicyclo[2.2.1]hept-2-yl]-2-heptenol Following the procedure of Examples 52 and 31 and Example 1 Parts A and B except substituting cyclopentyl carboxylic acid for 2-phenylpropionic acid in Example 1 Part A (1), the title compound is obtained.

EXAMPLE 57

(1α,2β,3β,4α)-7-[3-(3-Hydroxy-5-hexenyl)-7-oxabicyclo[2.2.1]hept-2-yl]-2-heptenol Following the procedure of Examples 52 and 31 and Example 1 Parts A and B except substituting 2-propenyl carboxylic acid for 2-phenylpropionic acid in Example 1 Part A (1), the title compound is obtained.

EXAMPLE 58

(1α,2β,3β,4α)-7-[3-(3-Hydroxy-1-octyl)-7-oxabicyclo[2.2.1]hept-2-yl]-2-heptenol

Following the procedure of Examples 52 and 31 and Example 1 Parts A and B except substituting pentane carboxylic acid for 2-phenylpropionic acid in Example 1 Part A (1), the title compound is obtained.

EXAMPLES 59 TO 72

Following the procedures outlined in the specification and described in the working Examples, the following additional compounds in accordance with the present invention may be prepared.

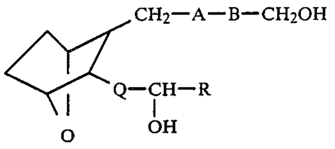

| Ex. No. | A | B | Q | R |
|---|---|---|---|---|
| 59. | $CH{=}CH{-}(CH_2)_2$ | $CH{=}CH$ | $(CH_2)_2$ | $C_3H_7$ |
| 60. | $CH{=}CH(CH_2)_4$ | — | $CH{=}CH$ | $C_6H_{13}$ |
| 61. | $CH{=}CH{-}(CH_2)_5$ | — | $(CH_2)_2$ | $C_2H_5$ |
| 62. | $CH{=}CH{-}(CH_2)_2$ | — | $CH{=}CH$ | $C_6H_5$ |
| 63. | $CH{=}CH{-}(CH_2)_3$ | $CH{=}CH$ | $(CH_2)_2$ | $C_6H_5CH_2{-}$ |
| 64. | $(CH_2)_4$ | $CH{=}CH$ | $CH{=}CH$ | 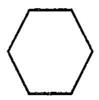 |
| 65. | $(CH_2)_3$ | $CH{=}CH$ | $(CH_2)_2$ | 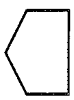 |
| 66. | $CH_2$ | $CH{=}CH$ | $CH{=}CH$ | 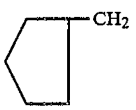 |
| 67. | $CH_2$ | — | $CH{=}CH$ | 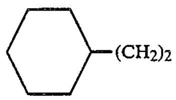 |
| 68. | $(CH_2)_4$ | — | $(CH_2)_2$ | $CH_3{-}CH{=}CH{-}CH_2{-}$ |
| 69. | $(CH_2)_6$ | — | $CH{=}CH$ | $CH_3{-}(CH_2)_2{-}CH{=}CH{-}$ |
| 70. | $CH{=}CH{-}CH_2$ | $CH{=}CH$ | $(CH_2)_2$ | $CH_3{-}CH{=}CH{-}$ |
| 71. | $CH{=}CH{-}(CH_2)_5$ | — | — | $C_4H_9$ |
| 72. | $(CH_2)_4$ | $CH{=}CH$ | $(CH_2)_2$ | $C_5H_{11}$ |

What is claimed is:

1. A compound having the structural formula

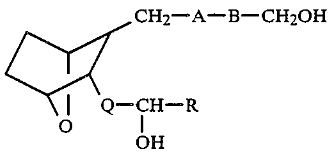

and including all stereoisomers thereof, wherein A is $—CH{=}CH—(CH_2)_n—$ or $(CH_2)_q$; B is $—CH{=}CH—$; n is 1 to 3; q is 1 to 4; Q is $—CH{=}CH—$ or $(CH_2)_2$; and R is lower alkyl, aryl, aralkyl, cycloalkyl, cycloalkylalkyl or lower alkenyl, wherein the term lower alkyl or alkyl by itself or as part of another group contains 1 to 12 carbons and is unsubstituted or substituted with halo, trifluoromethyl, alkoxy, aryl, alkyl-aryl, haloaryl, cycloalkyl or alkylcycloalkyl;

the term aryl by itself or as part of another group contains 6 to 10 carbons and is unsubstituted or substituted with 1 or 2 lower alkyl groups, 1 or 2 halogens and/or 1 or 2 lower alkoxy groups;

the term cycloalkyl by itself or as part of another group contains 3 to 12 carbons and is unsubstituted or substituted with 1 or 2 halogens, 1 or 2 lower alkyl groups and/or 1 or 2 lower alkoxy groups, the term lower alkenyl contains 2 to 12 carbons;

the term $(CH_2)_n$ includes 1 to 3 carbons in the normal chain and the term $(CH_2)_q$ includes 1 to 4 carbons in the normal chain;

and the terms $(CH_2)_2$, $(CH_2)_n$ and $(CH_2)_q$ may be unsubstituted or include one or more lower alkyl substituents.

2. The compound as defined in claim 1 wherein B is $—CH{=}CH—$ and A is $—CH{=}CH—(CH_2)_n$ and n is 1 to 3.

3. the compound as defined in claim 1 wherein B is $—CH{=}CH—$, A is $(CH_2)_1$ and q is 1 to 4.

4. The compound as defined in claim 1 wherein R is butyl, pentyl, hexyl, heptyl or 1,1-dimethylpentyl or methylbenzyl.

5. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

6. The method as defined in claim 8 wherein said compound is administered in an amount within the range of from about 1 to about 100 mg/kg.

7. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier thereof.

8. A method of inhibiting bronchoconstriction associated with asthma, which comprises administerihg to a mammalian host an effective amount of a compound as defined in claim 1 or a pharmaceutically acceptable salt thereof.

9. A method for treating peripheral vascular disease, which comprises topically or systemically administering to a mammalian host an effective amount of a compound as defined in claim 1 or a pharmaceutically acceptable salt thereof.

* * * * *

UNITED STATES PATENT AND TRADEMARK OFFICE

CERTIFICATE OF CORRECTION

PATENT NO. : 4,542,156

DATED : September 17, 1985

INVENTOR(S) : Jagabandhu Das et al.

It is certified that error appears in the above-identified patent and that said Letters Patent is hereby corrected as shown below:

Column 10, line 56, "yl]5" should read --yl]-5--.
Column 10, line 64, "yl]5" should read --yl]-5--.
Column 11, line 43, "2.2.1]" should read --[2.2.1]--.
Column 12, line 47, "[b" should read --[--.
Column 12, line 17, "(E)" should read --(Z)--.
Column 13, line 20, "2.2.1]" should read --[2.2.1]--.
Column 13, line 28, "1α,2β," should read --(1α,2β,--.
Column 13, line 47, "oxabicyclo" should read --7-oxabicyclo--.
Column 13, line 64, "2.2.1]" should read --[2.2.1]--.
Column 13, line 67, "-phenylpropi-" should read --2-phenylpropi- --.
Column 14, line 4, "oxabicyclo" should read --7-oxabicyclo--.
Column 14, line 21, "(4S" should read --(4S)--.
Column 15, line 2, "butyl)--" should read --butyl)-7- --.
Column 15, line 19, "2.2.1]" should read --[2.2.1]--.
Column 15, line 25, "[2.2.1" should read --[2.2.1]--.
Column 16, line 45, "[[1α" should read --[1α--.
Column 18, line 21, delete "at -78$^{o}$C.,".
Column 18, line 63, "3-(3" should read --[3-(3--.

UNITED STATES PATENT AND TRADEMARK OFFICE

CERTIFICATE OF CORRECTION

PATENT NO. : 4,542,156

DATED : September 17, 1985

INVENTOR(S) : Jagabandhu Das et al.

It is certified that error appears in the above-identified patent and that said Letters Patent is hereby corrected as shown below:

Column 20, line 19, "yl-" should read --yl]- --.
Column 20, line 26, "1β" should read --1α--.
Column 20, line 53, "2.2.1]" should read --[2.2.1]--.
Column 20, line 64, "7-3" should read --7-[3--.
Column 24, line 50, "$(CH_2)_1$" should read --$(CH_2)_q$--.
Column 25, line 2, "administerihg" should read --administering--.

Signed and Sealed this

Twenty-eighth Day of October, 1986

[SEAL]

*Attest:*

DONALD J. QUIGG

*Attesting Officer* *Commissioner of Patents and Trademarks*